(12) United States Patent
Hijihara

(10) Patent No.: US 10,278,567 B2
(45) Date of Patent: May 7, 2019

(54) ENDOSCOPE

(71) Applicant: OLYMPUS CORPORATION, Tokyo (JP)

(72) Inventor: Kunihiko Hijihara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/591,182

(22) Filed: May 10, 2017

(65) Prior Publication Data

US 2017/0238787 A1 Aug. 24, 2017

Related U.S. Application Data

(63) Continuation of application No. PCT/JP2016/060418, filed on Mar. 30, 2016.

(30) Foreign Application Priority Data

May 28, 2015 (JP) ................................ 2015-109047

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0011* (2013.01); *A61B 1/0057* (2013.01); *A61B 1/233* (2013.01); *G02B 23/24* (2013.01)

(58) Field of Classification Search
USPC ........................................................ 600/149
See application file for complete search history.

(56) References Cited

U.S. PATENT DOCUMENTS 3,880,148 A * 4/1975 Kanehira ........... A61B 1/00165
385/118
4,633,882 A * 1/1987 Matsuo ................ A61B 1/0052
600/146
(Continued)

FOREIGN PATENT DOCUMENTS

CN 202235277 U 5/2012
JP H07-178041 A 7/1995
(Continued)

OTHER PUBLICATIONS

International Search Report dated Jun. 21, 2016 issued in PCT/JP2016/060418.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope includes: an insertion portion including a bending portion bendable at least in a vertical direction on a distal end portion side; an operation portion to which a proximal end portion of the insertion portion is connected; a traction wire including a first end and a second end, connected to the insertion portion at the first end, and configured to bend the bending portion by being pulled; a fixing member fixed to the second end of the traction wire; a holding member configured to hold the fixing member; and a pulley turnably provided inside the operation portion and including a disposing portion where the holding member is disposed.

4 Claims, 8 Drawing Sheets

(51) Int. Cl.
 *G02B 23/24* (2006.01)
 *A61B 1/233* (2006.01)

(56) References Cited

U.S. PATENT DOCUMENTS

| | | | | |
|---|---|---|---|---|
| 4,688,555 A | * | 8/1987 | Wardle | A61B 1/0052 600/149 |
| 4,841,950 A | * | 6/1989 | Fukuda | A61B 1/0052 600/146 |
| 4,941,455 A | * | 7/1990 | Watanabe | A61B 1/0052 600/146 |
| 4,996,974 A | * | 3/1991 | Ciarlei | A61B 1/0052 138/120 |
| 5,167,221 A | * | 12/1992 | Chikama | A61B 1/0052 600/149 |
| 5,752,912 A | * | 5/1998 | Takahashi | A61B 1/0052 600/146 |
| 5,876,325 A | | 3/1999 | Mizuno et al. | |
| 6,491,627 B1 | * | 12/2002 | Komi | A61B 1/0052 600/146 |
| 6,702,737 B2 | * | 3/2004 | Hino | A61B 1/0052 600/146 |
| 8,777,839 B2 | * | 7/2014 | Kondoh | A61B 1/00071 600/101 |
| 8,911,362 B2 | * | 12/2014 | Kaneko | A61B 1/00066 356/241.6 |
| 2005/0054899 A1 | * | 3/2005 | Miyake | A61B 1/0052 600/152 |
| 2005/0272975 A1 | * | 12/2005 | McWeeney | A61B 1/00071 600/113 |
| 2007/0208375 A1 | | 9/2007 | Nishizawa et al. | |
| 2008/0139886 A1 | * | 6/2008 | Tatsuyama | A61B 1/0055 600/146 |
| 2008/0306339 A1 | * | 12/2008 | Hashimoto | A61B 1/0052 600/114 |
| 2009/0192357 A1 | * | 7/2009 | Torii | A61B 1/0052 600/149 |
| 2010/0198253 A1 | * | 8/2010 | Jinno | A61B 17/29 606/205 |
| 2012/0046522 A1 | | 2/2012 | Naito | |
| 2012/0220832 A1 | * | 8/2012 | Nakade | A61B 1/0052 600/149 |
| 2013/0038930 A1 | * | 2/2013 | Vent | A61B 1/0052 359/362 |
| 2014/0121462 A1 | * | 5/2014 | Okamoto | A61B 1/0052 600/149 |
| 2016/0113481 A1 | * | 4/2016 | Okamoto | A61B 1/0052 600/132 |
| 2016/0374536 A1 | * | 12/2016 | Osaki | A61B 1/0052 600/148 |
| 2018/0071040 A1 | * | 3/2018 | Haraguchi | A61B 1/00 |

FOREIGN PATENT DOCUMENTS

| | | |
|---|---|---|
| JP | 2001-061770 A | 3/2001 |
| JP | 2005-218569 A | 8/2005 |
| JP | 2007-190047 A | 8/2007 |
| JP | 2009-189684 A | 8/2009 |
| JP | 2011-177383 A | 9/2011 |
| JP | 2012-249862 A | 12/2012 |
| WO | WO 2016/027521 A1 | 2/2016 |

OTHER PUBLICATIONS

Partial Supplementary European Search Report dated Jun. 1, 2018 in European Patent Application No. 16 79 9672.7.

* cited by examiner

ENDOSCOPE

CROSS REFERENCE TO RELATED APPLICATION

This application is a continuation application of PCT/JP2016/060418 filed on Mar. 30, 2016 and claims benefit of Japanese Application No. 2015-109047 filed in Japan on May 28, 2015, the entire contents of which are incorporated herein by this reference.

BACKGROUND OF THE INVENTION

1. Field of the Invention

The present invention relates to an endoscope including a bending lever for pulling and loosening a bending wire in an operation portion.

2. Description of the Related Art

An endoscope which allows observation or the like by inserting an elongated insertion portion into a subject is widely utilized. There is a type of endoscope which includes a bending portion on a distal end side of the insertion portion. The bending portion is generally configured to perform a bending operation by pulling and loosening a bending wire by turning a bending lever, for example, which is a bending operation device provided in the operation portion.

For example, in an endoscope apparatus in Japanese Patent Application Laid-Open Publication No. 2005-218569, a bending wire configured by connecting a traction wire on one side and a traction wire on another side by a wire connecting mechanism is illustrated. The wire connecting mechanism is configured by a male screw pipe sleeve to which an end portion of the traction wire on one side is fixed, and a female screw pipe sleeve to which an end portion of the traction wire on the other side is fixed, and the bending wire is configured by uniting the male screw pipe sleeve and the female screw pipe sleeve by screwing.

According to the configuration, tension of the bending wire can be adjusted by adjusting a screwing amount of the male screw pipe sleeve and the female screw pipe sleeve.

In a case of providing the wire connecting mechanism provided in a drum portion illustrated in Japanese Patent Application Laid-Open Publication No. 2005-218569 inside the operation portion of the endoscope illustrated in Japanese Patent Application Laid-Open Publication No. 2007-190047 or inside the operation portion of the endoscope illustrated in Japanese Patent Application Laid-Open Publication No. 2009-189684 for example, disposition inside the operation portion illustrated in Japanese Patent Application Laid-Open Publication No. 2007-190047 is relatively easy.

SUMMARY OF THE INVENTION

An endoscope of one aspect of the present invention includes: an insertion portion including a bending portion bendable at least in a vertical direction on a distal end portion side; an operation portion to which a proximal end portion of the insertion portion is connected; a traction wire including a first end and a second end, connected to the insertion portion at the first end, and configured to bend the bending portion by being pulled; a fixing member fixed to the second end of the traction wire; a holding member configured to hold the fixing member; and a pulley turnably provided inside the operation portion and including a disposing portion where the holding member is disposed, and the pulley includes a screw receiving member disposing space as the disposing portion including a notched surface where a screw receiving member as the holding member to which a screw member as the fixing member is screwed and arranged is arranged, and a through-hole including openings respectively on a bottom surface of a circumferential groove and the notched surface.

An endoscope of one aspect of the present invention includes: an insertion portion including a bending portion bendable at least in a vertical direction on a distal end portion side; an operation portion to which a proximal end portion of the insertion portion is connected; a traction wire including a first end and a second end, connected to the insertion portion at the first end, and configured to bend the bending portion by being pulled; a fixing member fixed to the second end of the traction wire; a holding member configured to hold the fixing member; and a pulley turnably provided inside the operation portion and including a disposing portion where the holding member is disposed, and the pulley includes a rotating body accommodating portion as the disposing portion where a rotation adjusting member in a columnar shape as the holding member configured to house a pin as the fixing member is turnably arranged, and a notch configured to notch a portion of a circumferential groove communicating the rotating body accommodating portion with an outside.

DETAILED DESCRIPTION OF THE PREFERRED EMBODIMENT(S)

Figure 1:
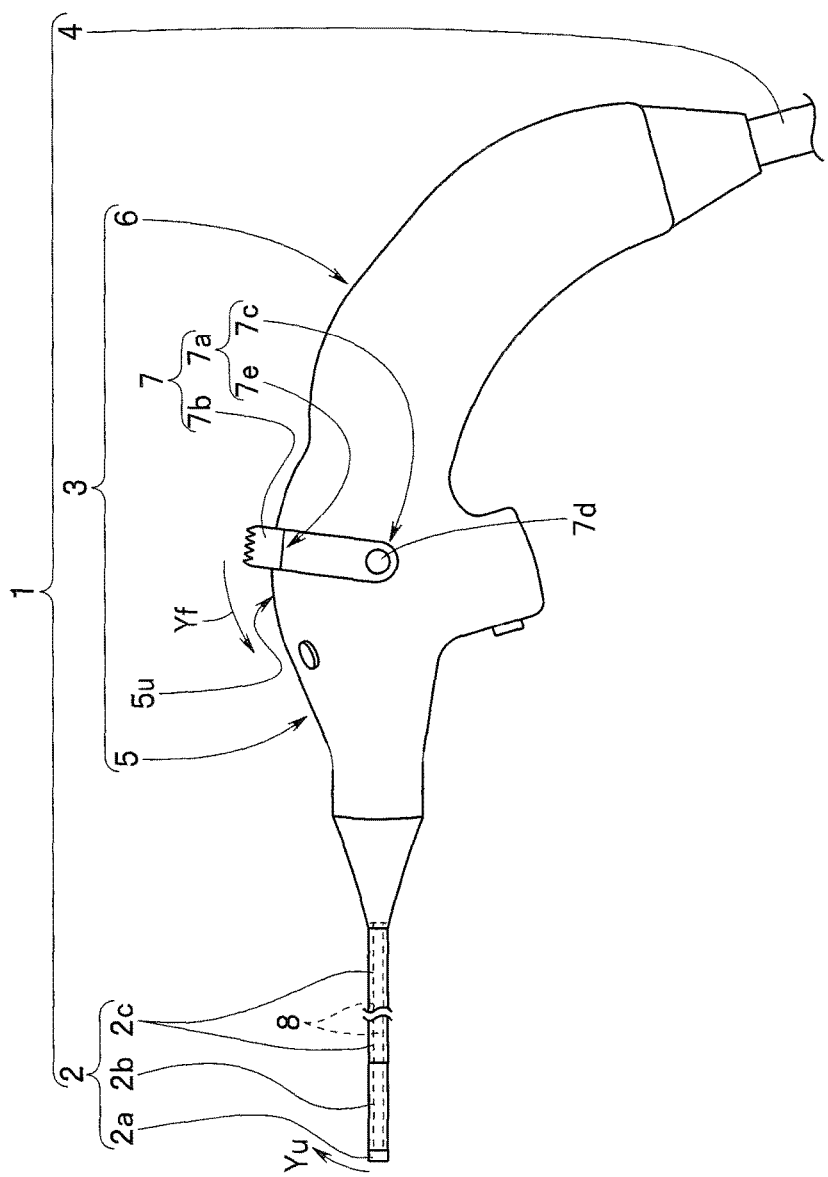
FIG. 1 is a diagram explaining an endoscope, and is one side view of the endoscope.

Hereinafter, embodiments of the present invention will be described with reference to the drawings.

Note that, in some of the individual drawings used in following descriptions, a scale is made different for each component in order to turn the individual components to such sizes that the components can be recognized on the drawings. That is, the present invention is not limited only to quantities of the components, shapes of the components, ratios of the sizes of the components, and relative positional relationships of the individual components described in the drawings.

A first embodiment will be described with reference to FIG. 1 to FIG. 4C.

As illustrated in FIG. 1, an endoscope 1 is configured mainly including an insertion portion 2, a grasping operation portion 3, and a universal cable 4. The grasping operation portion 3 is configured by integrally fixing an operation portion 5 and an extension portion 6.

The insertion portion 2 is inserted into a nasal cavity, for example. The insertion portion 2 is configured by connecting, in order from the distal end side, a distal end portion 2a, a bending portion 2b, and a flexible tube portion 2c. Inside the distal end portion 2a, an image pickup apparatus (not shown in the figure) including an image pickup device such as a CCD or a C-MOS configured to pick up an image of a subject portion is incorporated.

In addition, the configuration may be such that an image guide fiber is provided in the distal end portion 2a instead of the image pickup device.

The bending portion 2b is configured to bend in a vertical direction for example. The flexible tube portion 2c has such flexibility that the flexible tube portion 2c is deformable along the nasal cavity in a state that the insertion portion 2 is inserted into the nasal cavity.

On a proximal end side of the insertion portion 2, the operation portion 5 is connected. The operation portion 5 is provided with a bending lever 7. The bending lever 7 is positioned near the extension portion 6 which is the proximal end side of the operation portion 5.

The bending lever 7 is configured in a roughly L shape, and includes a lever body 7a and a finger pad 7b. The lever body 7a includes a first end and a second end, and one end portion of a turning shaft member 7d is integrally fixed to a first end portion 7c. Then, the lever body 7a is turnably disposed on one side face side of the operation portion 5.

By rotationally moving the finger pad 7b of the bending lever 7 in a direction of an arrow Yf, a bending wire 8 is pulled and loosened and the bending portion 2b is bent in the direction of an arrow Yu (an upper side of the drawing).

Note that the configuration may be such that the bending portion 2b is bent in an upper direction by rotationally moving the bending lever 7 in a direction opposite to the direction of the arrow Yf.

In addition, the bending lever may be a so-called joystick-like lever. In a case of the joystick-like lever, the lever can be tilted in all directions including not only the vertical direction but also a horizontal direction.

In addition, the bending portion may be bendable in all the directions including not only the vertical direction but also the horizontal direction.

The bending wire 8 described above is one traction wire including the first end and the second end. In the present embodiment, the bending wire 8 is two of an upper bending wire 8u and a lower bending wire 8d. Then, the first ends of the bending wires 8u and 8d are respectively connected to a predetermined position of a most distal end piece (not shown in the figure) configuring the bending portion 2b of the insertion portion 2.

Figure 2:
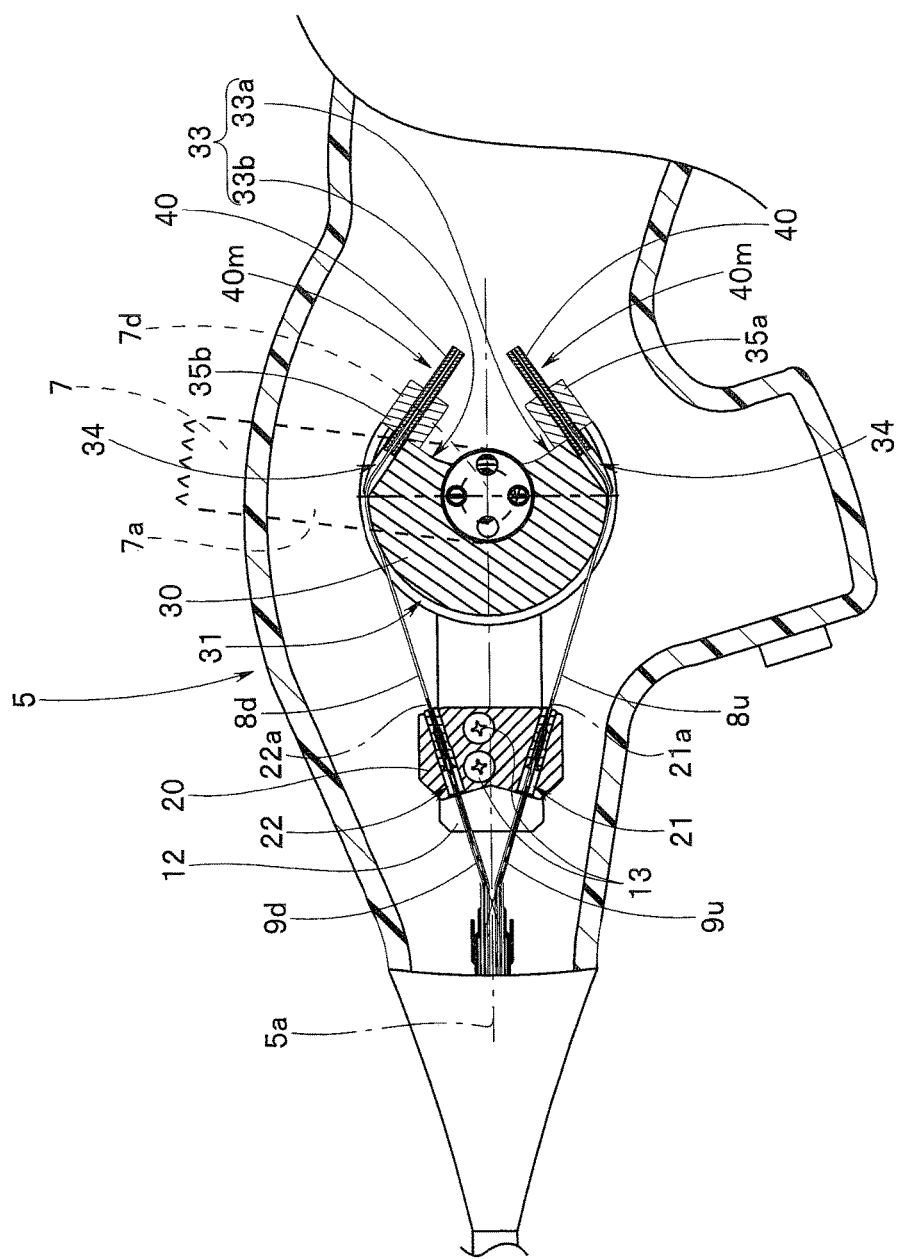
FIG. 2 is a diagram mainly explaining a pulley and a bending wire provided inside an operation portion of a grasping operation portion of the endoscope.

As illustrated in FIG. 2, the bending wires 8u and 8d are guided into the operation portion 5.

A support plate 12 is provided inside the operation portion 5, and a wire guide member 20 and a pulley 30 are mainly disposed on the support plate 12. The support plate 12 is fixed inside the operation portion 5, and divides a space inside the operation portion into a space portion where the bending wires 8u and 8d are inserted and arranged, and a space portion where an image pickup cable, a signal cable and various kinds of tubes not shown in the figure are inserted and arranged.

The wire guide member 20 is integrally fixed on one surface of the support plate 12 by a fixing screw 13. On the wire guide member 20, an upper wire guide groove (may be a guide hole) 21 and a lower wire guide groove 22 are formed.

Inside the guide grooves 21 and 22, proximal end portions of wire guide pipes 9u and 9d for example are fixed. Center lines 21a and 22a of the guide grooves 21 and 22 are inclined at a predetermined angle to a longitudinal axis 5a of the operation portion 5.

The bending wires 8u and 8d led out from an inside of the wire guide pipes 9u and 9d of the guide grooves 21 and 22 are wound and arranged along a circumferential groove 31 of the pulley 30 after wire middle portions are brought into contact with the circumferential groove 31.

The pulley 30 is turnably arranged on one surface of the support plate 12. Specifically, the pulley 30 is integrally fixed to a middle portion of the turning shaft member 7d. The turning shaft member 7d is turnably held by the support plate 12.

Therefore, by rotating the bending lever 7 clockwise or counterclockwise, the turning shaft member 7d integrally fixed to the lever body 7a and the pulley 30 integrally fixed to the turning shaft member 7d are rotated in the same direction.

Figure 3A:
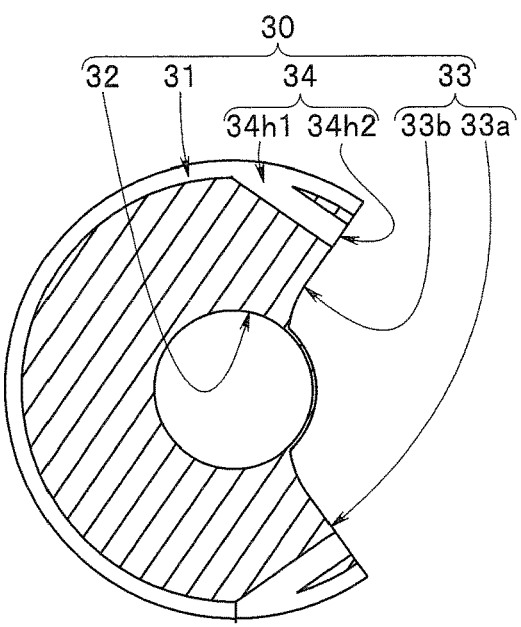
FIG. 3A is a diagram explaining the pulley.

As illustrated in FIG. 3A, the pulley 30 is a pulley member including a roughly V-shaped notched portion on a disk.

The pulley 30 includes the circumferential groove 31, a shaft hole 32, a notched portion 33, and an adjustment hole 34.

The circumferential groove 31 is a recessed groove formed on an outer peripheral surface of the pulley 30. The middle portions of the bending wires 8u and 8d are wound and arranged in the circumferential groove 31, and the wires 8u and 8d are prevented from falling out from the pulley 30.

The shaft hole 32 is a center through-hole, and the middle portion of the turning shaft member 7d is arranged and integrally fixed to the pulley 30.

The notched portion 33 is a disposing portion, and is a screw receiving member disposing space for fixing a pair of screw receiving members 35a and 35b to be described later. Notched surfaces 33a and 33b configuring the notched portion 33 are disposing surfaces, and one surface in a longitudinal direction of the screw receiving members 35a and 35b is fixed and arranged.

The adjustment hole 34 is a through-hole including a first opening 34h1 on a bottom surface of the circumferential groove 31 and including a second opening 34h2 respectively on the notched surfaces 33a and 33b. Inside the adjustment hole 34, second ends of the bending wires 8u and 8d including screwing members 40 are inserted and arranged.

As illustrated in FIG. 2, the screwing member 40 is fixed beforehand as a fixing member to the second end of each of the respective bending wires 8u and 8d. The screwing member 40 is a columnar body provided with a male screw 40m on the outer peripheral surface, and is set to a predetermined length.

Figure 3B:
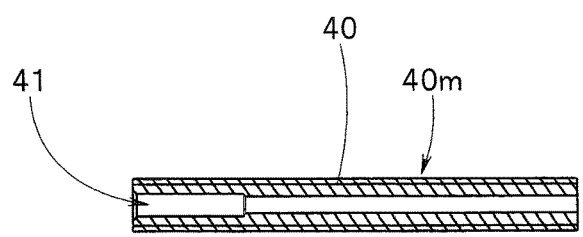
FIG. 3B is a diagram explaining a screw member which is one configuration example of a fixing member.

As illustrated in FIG. 3B, the screwing member 40 is provided with a wire disposing hole 41 which is a through-hole formed along a center axis. Each of the second ends of the bending wires 8u and 8d is arranged inside the wire disposing hole 41, and integrally bonded to the screwing member 40 by solder for example.

Figure 3C:
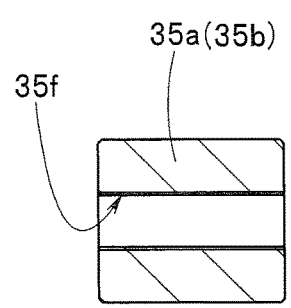
FIG. 3C is a diagram explaining a screw receiving member which is one configuration example of a holding member.

As illustrated in FIG. 3C, the screw receiving members 35a and 35b are holding members, are hexagonal pillar members for example, and are set to the predetermined length. At each of the screw receiving members 35a and 35b, a female screw 35f to which the screwing member 40 is to be screwed is formed over an entire length in the longitudinal direction.

Note that the screwing member 40 is loosely arranged to the adjustment hole 34. In addition, the screw receiving members 35a and 35b are not limited to a hexagonal shape, and may be a columnar shape or a quadrangular prism shape or the like. In the columnar shape, one plane and another plane positioned on an opposite side of the one plane are provided on the outer peripheral surface.

Here, assembly of the bending wires 8u and 8d to the pulley 30 will be described.

Note that a procedure of assembling the upper bending wire 8u to the pulley 30 will be described here, and for the assembly of the lower bending wire 8d to the pulley 30 in a similar assembly procedure, the description is omitted.

Figure 4A:
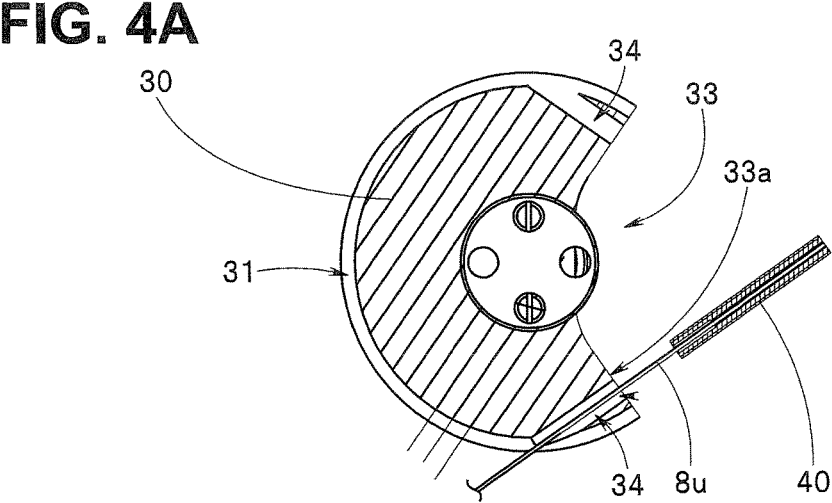
FIG. 4A is a diagram explaining a state of leading out a second end of the bending wire including the screw member into a notched portion.

An operator first inserts the screwing member 40 fixed to the second end of the upper bending wire 8u from an opening on a side of the circumferential groove 31 into the adjustment hole 34. Then, as illustrated in FIG. 4A, the second end of the upper bending wire 8u including the screwing member 40 is led out from an opening on the side of the notched surface 33a into the notched portion 33.

Figure 4B:
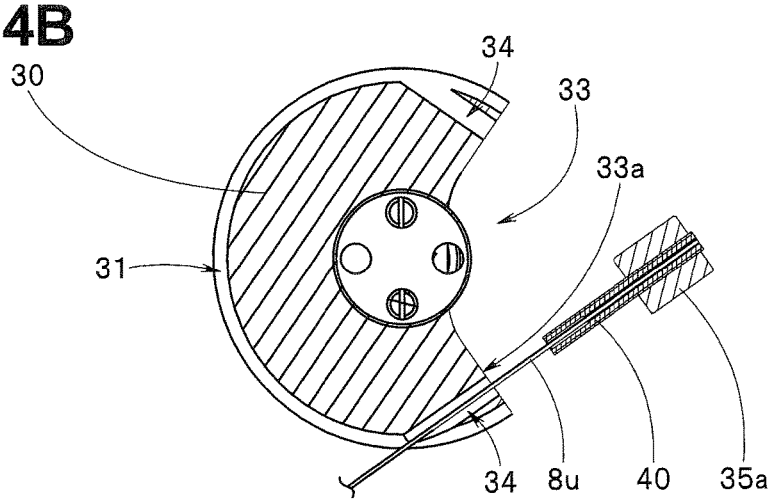
FIG. 4B is a diagram explaining a state of screwing the screw receiving member to the screw member.

Next, the operator screws the screw receiving member 35a to the screwing member 40 and attaches the upper bending wire 8u to the pulley 30 as illustrated in FIG. 4B. Thus, the upper bending wire 8u is prevented from falling out from the pulley 30.

Figure 4C:
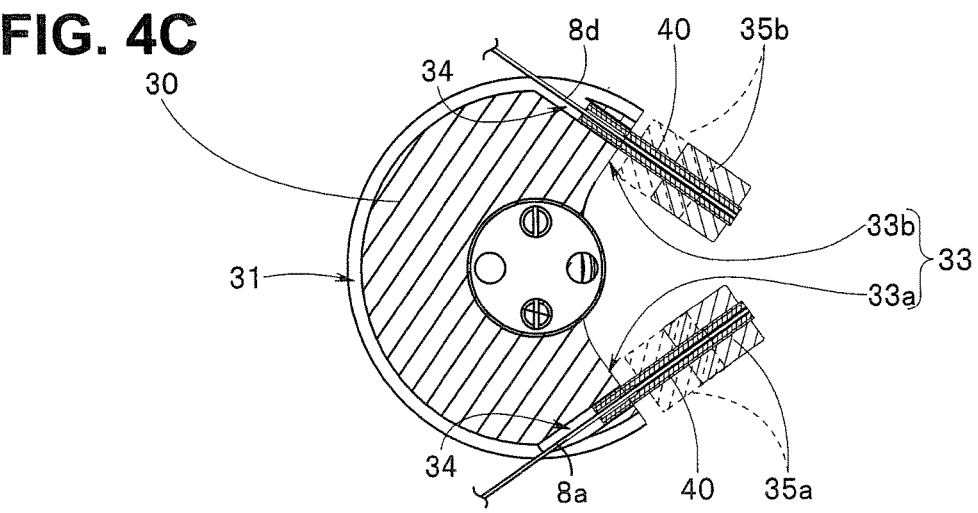
FIG. 4C is a diagram explaining tension adjustment, and is a diagram explaining a state of moving the screw receiving member screwed to the screw member.

Next, the operator leads out the second end of the lower bending wire 8d including the screwing member 40 from the opening on the side of the notched surface 33a similarly to the above description, screws the screw receiving member 35b to the screwing member 40 and attaches the lower bending wire 8d to the pulley 30 as illustrated in FIG. 4C.

Thereafter, while adjusting an arranging position of the screwing member 40 by rotationally moving the screw receiving member 35a to the screwing member 40 as illustrated by a broken line and adjusting tension of the upper bending wire 8u, the operator adjusts the arranging position of the screwing member 40 by rotationally moving the screw receiving member 35b also as illustrated by the broken line and also adjusts the tension of the lower bending wire 8d.

Next, after tension adjustment of the bending wires 8u and 8d is completed, the operator applies an adhesive agent for example. As a result, the screw receiving members 35a and 35b are integrally fixed to the notched surfaces 33a and 33b, and the screwing members 40 fixed to the bending wires 8u and 8d are integrally fixed to the screw receiving members 35a and 35b.

As a result, the assembly of the bending wires 8u and 8d to the pulley 30 is completed.

In this way, by screwing and arranging the screwing members 40 fixed to the second ends of the bending wires 8u and 8d to the screw receiving members 35a and 35b provided inside the notched portion 33 of the pulley 30, the bending wires 8u and 8d can be easily attached to the pulley 30 regardless of a length of the operation portion 5.

In addition, by rotating the screw receiving members 35a and 35b and adjusting the arranging positions of the screw receiving members 35a and 35b and the screwing members 40, the tension of the bending wires 8u and 8d can be set to a predetermined state.

Note that, in the above description, an aspect of fixing the bending wire to the pulley is described. However, when the bending lever is a joystick-like lever, the bending wire is fixed to a predetermined position of a plate member to be tilted accompanying a tilting operation of the joystick-like lever. In this case, by bonding the screw member to an end portion of the bending wire, inserting the bonded screw member to a hole provided on the plate member, and screwing the screw member to the screw receiving member, the bending wire can be assembled to the plate member while adjusting the tension of the bending wire.

In the embodiment described above, after the tension adjustment of the bending wires 8u and 8d is completed, the adhesive agent is applied, the screw receiving members 35a and 35b are integrally fixed to the notched surfaces 33a and 33b, and also the screwing members 40 are integrally fixed to the screw receiving members 35a and 35b. However, as illustrated in FIG. 5B, heat-shrinkable tubes 36 may be provided to perform integral fixation.

Figure 5A:
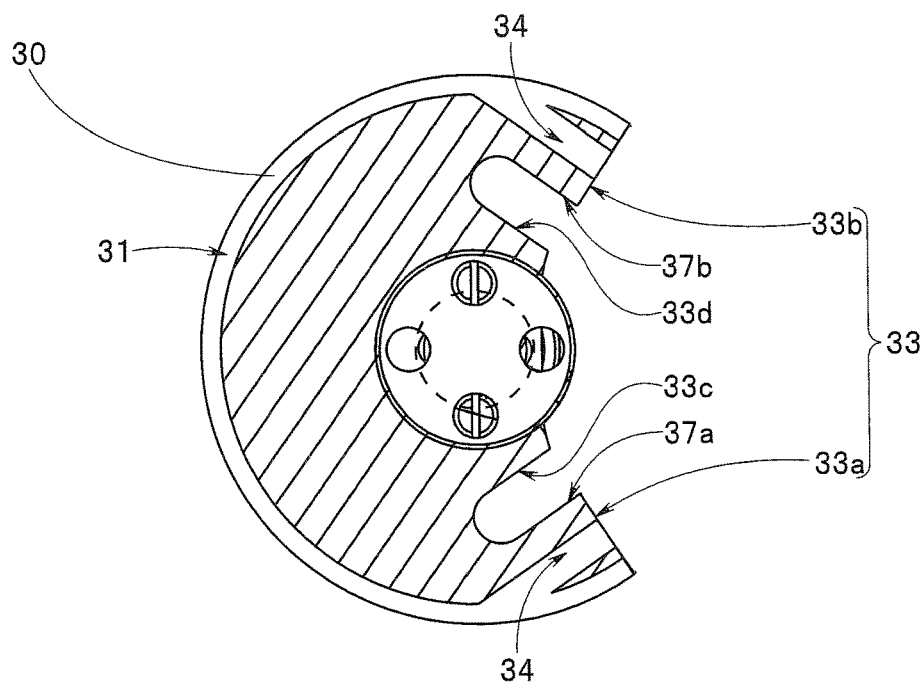
FIG. 5A explains the pulley to which a heat-shrinkable tube can be disposed.
Figure 5B:
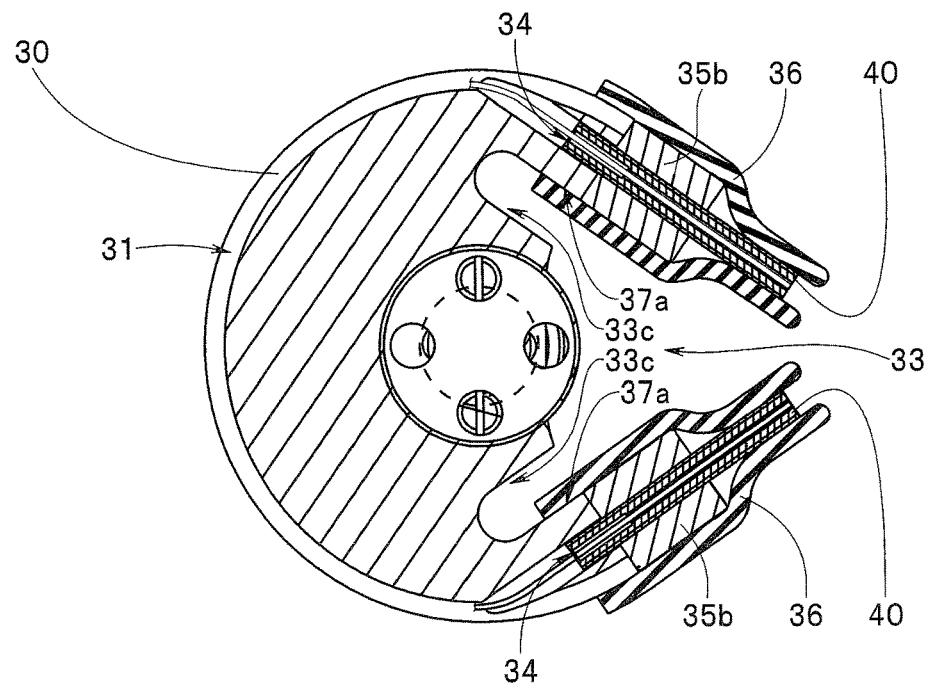
FIG. 5B is a diagram illustrating the screw receiving member and the screw member provided in the pulley by the heat-shrinkable tube.

In the case of using the heat-shrinkable tubes 36, as illustrated in FIG. 5A, recessed portions 33c and 33d are provided on a periphery a predetermined distance away from the center of the adjustment hole 34 of the pulley 30, and projected portions 37a and 37b for tube installation are formed.

According to the configuration, after the tension adjustment of the bending wires 8u and 8d is completed, the operator installs the heat-shrinkable tubes 36 at the screw receiving members 35a and 35b and the projected portions 37a and 37b for the tube installation, and shrinks the heat-shrinkable tubes 36 by blowing hot air to the heat-shrinkable tubes 36 for example in the installation state.

As a result, by using the heat-shrinkable tubes 36, the screw receiving members 35a and 35b can be integrally fixed to the projected portions 37a and 37b for tube installation, and also the screwing members 40 can be integrally fixed to the screw receiving members 35a and 35b.

Then, according to the configuration, in the case that the bending wires 8u and 8d stretch due to secular change, the operator can easily perform readjustment of the tension or the like by opening the operation portion 5 and cutting off the heat-shrinkable tubes 36.

A second embodiment will be described with reference to FIG. 6 to FIG. 8C.

In the embodiment described above, the fixing member is the screw member, the holding member is the screw receiving member, and the screw receiving member to which the screw member is screwed and arranged is fixed to the notched surface.

Figure 6:
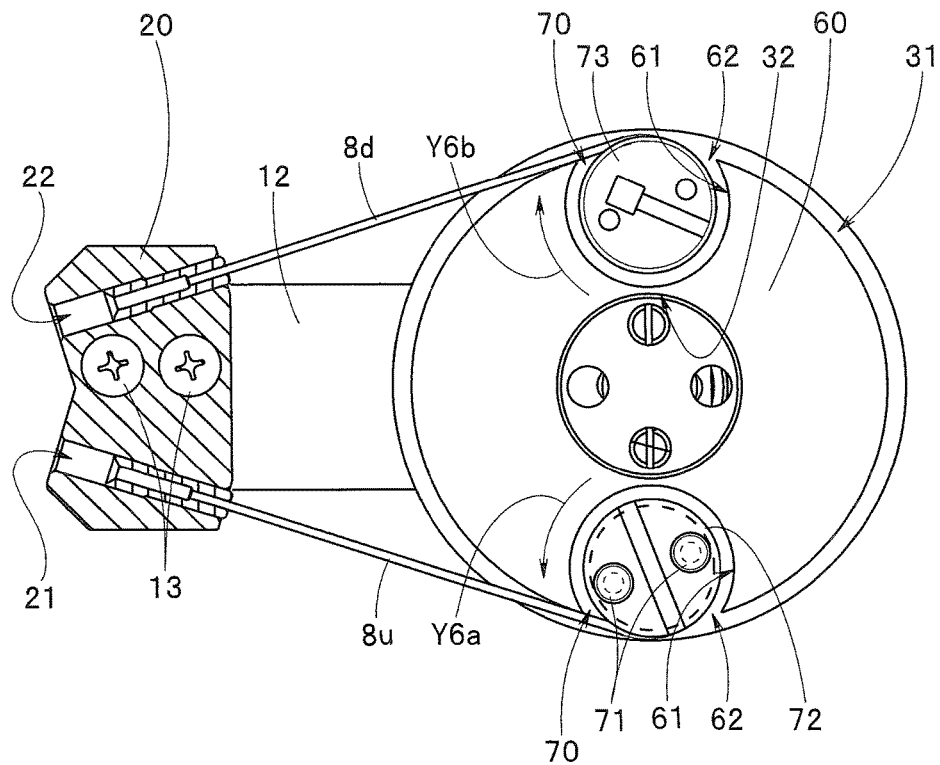
FIG. 6 is a diagram explaining the pulley including a rotating body accommodating portion, which is another configuration example of the pulley.
Figure 7:
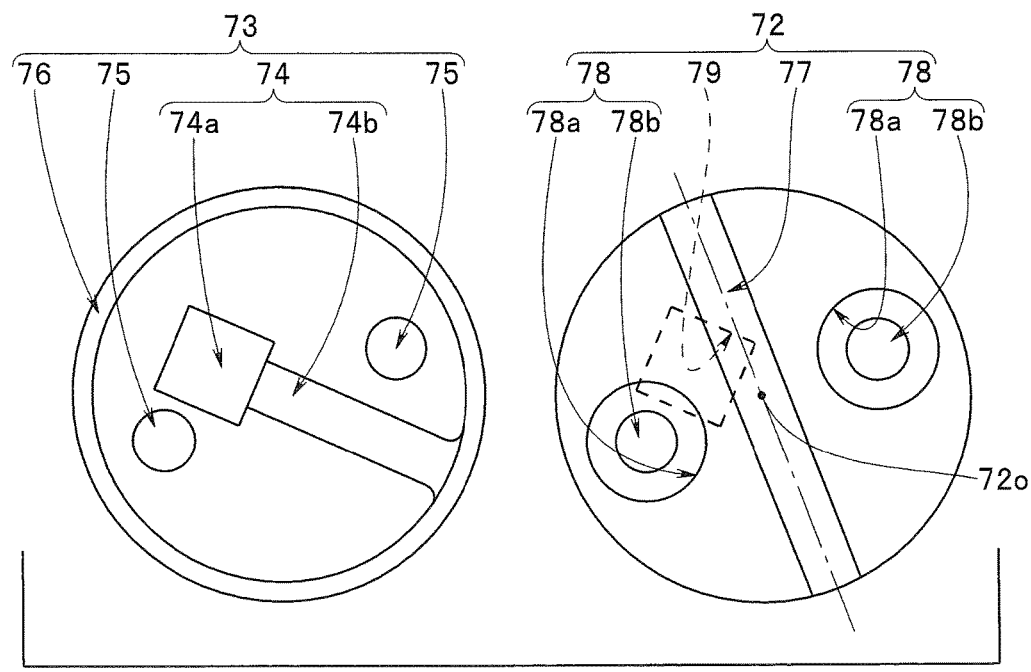
FIG. 7 is a diagram explaining a holding member and a fixing member arranged in the rotating body accommodating portion of the pulley.

However, the pulley, the fixing member and the holding member may be configured as illustrated in FIG. 6 to FIG. 8 below.

Note that, in the following description, same signs are attached to same members as the members in the embodiment described above, and the description is omitted.

As illustrated in FIG. 6, a pulley 60 in the present embodiment is provided with a pair of rotating body accommodating portions 61 which are circular recessed portions. The rotating body accommodating portion 61 is a disposing portion, and a rotation adjusting member 70 in a columnar shape which is a holding member is disposed inside the rotating body accommodating portion 61. The rotation adjusting member 70 is fixed to the rotating body accommodating portion 61 by a fixing screw 71.

An inner diameter of the rotating body accommodating portion 61 is set to be larger than an outer diameter of the rotation adjusting member 70 by a predetermined dimension. Therefore, inside the rotating body accommodating portion 61, the rotation adjusting member 70 is turnable.

Note that a sign 62 is a notch, and a portion of the rotation adjusting member 70 is exposed to an outside. For the notch 62, a portion of the circumferential groove 31 is notched so as to communicate the rotating body accommodating portion 61 with the outside.

The rotation adjusting member 70 includes a lid body 72 in a columnar shape and a rotating main body 73 in a columnar shape as illustrated in FIG. 6 and FIG. 7, and the rotation adjusting member 70 is configured by mounting and uniting the lid body 72 on a surface of the rotating main body 73.

In FIG. 6, a sign 72 is the lid body, a sign 73 is the rotating main body 73, and a state is that the lid body 72 of the rotation adjusting member 70 is detached and the surface of the rotating main body 73 is exposed.

An outer diameter of the lid body 72 and an outer diameter of the rotating main body 73 are same diameters.

As illustrated in FIG. 7, on the rotating main body 73, a fixing member disposing hole 74 having an opening on a surface, and female screw holes 75 which are a pair of through-holes having openings on the surface and a back surface are formed. On the outer peripheral surface of the rotating main body 73, a step portion 76a to be a wire disposing groove 76 where the bending wires 8u and 8d are to be wound is formed.

Inside the female screw holes 75, fixing screws 71 are screwed and arranged.

Figure 8A:
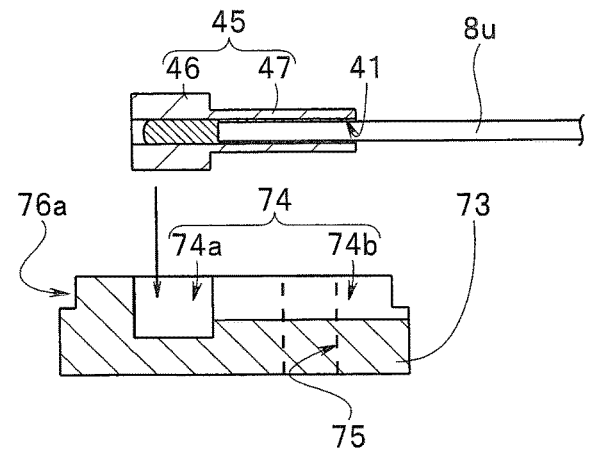
FIG. 8A is a diagram explaining assembly of a stepped pin to a rotating main body.

Inside the fixing member disposing hole 74, a stepped pin 45 which is a fixing member and is illustrated in FIG. 8A is disposed. The stepped pin 45 includes a large diameter portion 46 and a small diameter portion 47, and the small diameter portion 47 is communicated with the outside by notching the bottom surface of the step portion 76a.

The stepped pin 45 includes the wire disposing hole 41. Note that a columnar pin without a step may be used instead of the stepped pin 45.

In the present embodiment, the stepped pin 45 is integrally bonded to the second end of each of the bending wires 8u and 8d similarly to the screwing member 40 described above.

As illustrated in FIG. 7, the fixing member disposing hole 74 includes a large diameter recessed portion 74a and a small diameter recessed portion 74b. The small diameter portion 47 of the stepped pin 45 is arranged at the small diameter recessed portion 74b, and the large diameter portion 46 is arranged at the large diameter recessed portion 74a.

On the other hand, on the surface of the lid body 72, a groove 77 of a predetermined width and a pair of screw holes 78 are provided. The groove 77 is formed such that a center line of the groove 77 passes through a center 72o. At the groove 77, a distal end of a flathead screwdriver for example used when rotating the rotation adjusting member 70 is arranged.

The screw hole 78 includes a large diameter hole 78a and a small diameter hole 78b. A head portion (sign 71a in FIG. 8C) of the fixing screw 71 is arranged in the large diameter hole 78a, and a male screw portion (sign 71b in FIG. 8C) is inserted and arranged in the small diameter hole 78b.

On the back surface of the lid body 72 which is a mounting surface to be mounted on the surface of the rotating main body 73, a recessed portion 79 for housing the large diameter portion 46 of the stepped pin 45 is formed. The recessed portion 79 is a recessed portion for positioning the lid body 72 and the rotating main body 73.

Here, the assembly of the bending wires 8u and 8d to the pulley 60 will be described.

Note that a procedure of assembling the upper bending wire 8u to the pulley 60 will be described here, and for the assembly of the lower bending wire 8d to the pulley 60 in the similar assembly procedure, the description is omitted.

Figure 8B:
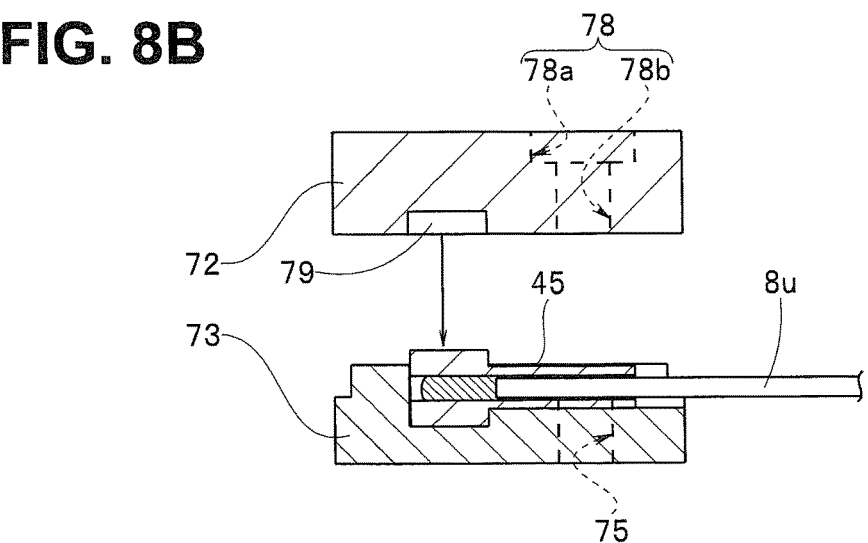
FIG. 8B is a diagram explaining assembly of a lid body to the rotating main body.

The operator first disposes the stepped pin 45 fixed to the second end of the upper bending wire 8u inside the fixing member disposing hole 74 of the rotating main body 73 as illustrated in FIG. 8A. Then, a portion of the large diameter portion 46 of the stepped pin 45 is turned to the state of protruding from the surface of the rotating main body 73 as illustrated in FIG. 8B.

Next, the operator mounts the lid body 72 on the surface of the rotating main body 73. At the time, the recessed portion 79 is put on the large diameter portion 46 of the stepped pin 45 protruding from the surface of the rotating main body 73. As a result, the rotation adjusting member 70 is configured in which the small diameter hole 78b and the female screw hole 75 are in an opposing positional relation and the stepped pin 45 is housed.

Figure 8C:
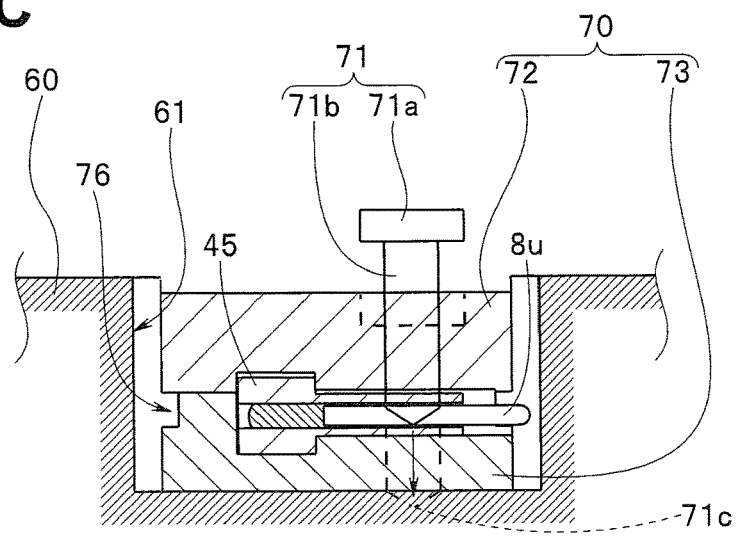
FIG. 8C is a diagram explaining assembly of a rotation adjusting member to the rotation body accommodating portion.

In addition, the step portion 76a is configured as the wire disposing groove 76 as illustrated in FIG. 8C, and the upper bending wire 8u is arranged inside the wire disposing groove 76.

Next, the operator screws the two fixing screws 71 to the two female screw holes 75 of the rotating main body 73 through the screw holes 78 of the lid body 72 respectively. Thereafter, the operator disposes the rotation adjusting member 70 inside the rotating body accommodating portion 61. Thus, the upper bending wire 8u is attached to the pulley 30.

Next, the operator attaches the lower bending wire 8d to the pulley 30 similarly to the above description.

Thereafter, the operator adjusts the tension by arranging the distal end of the flathead screwdriver for example at the groove 77, rotating one rotation adjusting member 70 in the direction of an arrow Y6a in FIG. 6, rotating the other rotation adjusting member 70 in the direction of an arrow Y6b, and winding the bending wires 8u and 8d.

As a result, the tension of the upper bending wire 8u and the tension of the lower bending wire 8d can be adjusted to the predetermined state.

Next, after the tension adjustment of the bending wires 8u and 8d is completed, the operator fastens the fixing screws 71. Then, the fixing screw 71 is moved to a position indicated by the broken line in FIG. 8C, a sharp distal end 71c enters the bottom surface of the rotating body accommodating portion 61, and the rotation adjusting member 70 is integrally fixed to the pulley 60.

As a result, the assembly of the bending wires 8u and 8d to the pulley 60 is completed.

In this way, the stepped pins 45 fixed to the second ends of the bending wires 8u and 8d are disposed to the rotation adjusting members 70, and the rotation adjusting members 70 are disposed to the rotating body accommodating portions 61 of the pulley 60. As a result, the bending wires 8u and 8d can be easily attached to the pulley 60 regardless of the length of the operation portion 5.

In addition, by rotating the rotation adjusting members 70 and increasing, decreasing and adjusting the winding amount of the bending wires 8u and 8d wound and arranged in the wire disposing grooves 76, the tension of the bending wires 8u and 8d can be set to the predetermined state.

Further, in the case that the bending wires 8u and 8d stretch due to the secular change, the operator can easily readjust the tension of the bending wires 8u and 8d by opening the operation portion 5, loosening the fixing screws 71 to cancel an integrally fixed state, then rotating the rotation adjusting members 70 and increasing the wire winding amount.

In addition, in the present embodiment, on a portion of the operation portion 5 corresponding to an outer side of the pulley 60, an attachable and detachable cover portion of about the same outer diameter as the outer diameter of the pulley 60 is provided. As a result, by detaching the cover portion from the operation portion 5, the rotation adjusting member 70 can be easily accessed, the tension of the bending wire can be readjusted, and repairability is improved.

Note that, after the adjustment, the fixing screws 71 are fastened similarly to the above description. At the time, since the rotation adjusting member 70 is rotationally moved, the distal end 71c of the fixing screw 71 enters a different position of the bottom surface of the rotating body accommodating portion 61, and the rotation adjusting member 70 is integrally fixed to the pulley 60.

In addition, in the embodiment described above, the configuration that the lid body 72 is provided with the recessed portion 79 is illustrated. However, need of the recessed portion 79 may be eliminated by making it possible to house the large diameter portion 46 inside the large diameter recessed portion 74a without letting a portion protruding from the surface of the rotating main body 73.

In addition, the lid body 72 and the rotating main body 73 may be united and the fixing member disposing hole may be formed through the united member.

A modification will be described with reference to FIG. 9A and FIG. 9B.

Figure 9A:
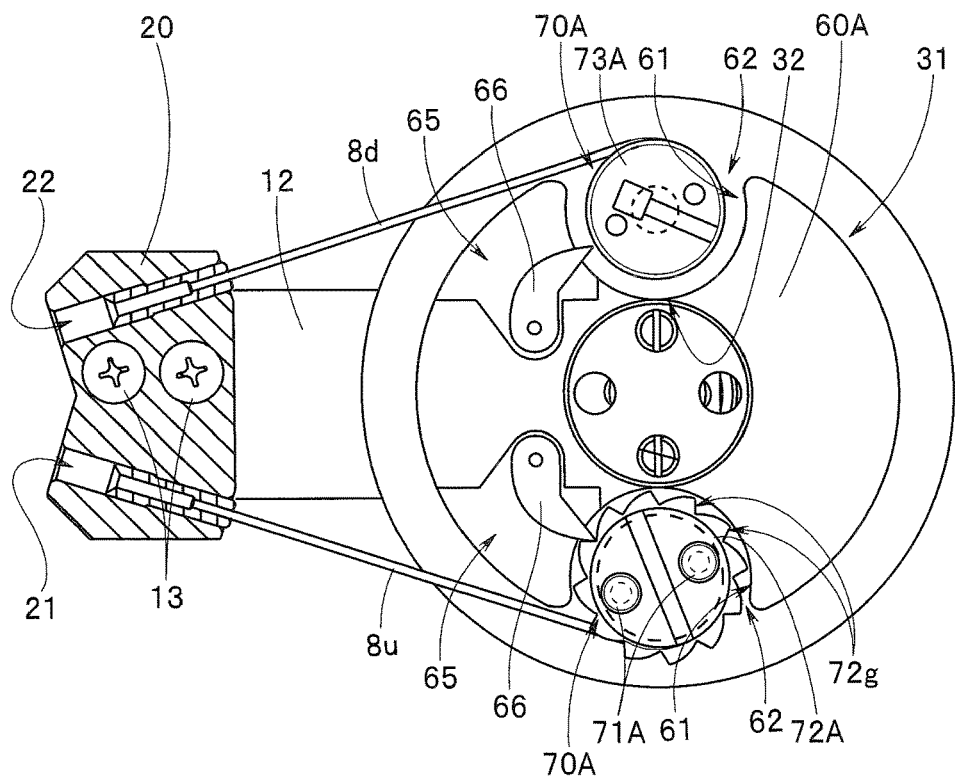
FIG. 9A is a diagram explaining another configuration of the pulley.

As illustrated in FIG. 9A, the lid body is turned to a lid body 72A with a ratchet gear in which a plurality of tooth portions 72g are arrayed in the circumferential direction of the outer peripheral surface, a pulley 60A is provided with a step portion 65, a stop claw 66 is turnably provided in the step portion 65, and the configuration including a ratchet mechanism is attained.

Note that the stop claw 66 is urged in a predetermined direction by a torsion spring (not shown in the figure) for example which is an urging member, is engaged with the tooth portions 72g, and restricts rotation in the predetermined direction.

Figure 9B:
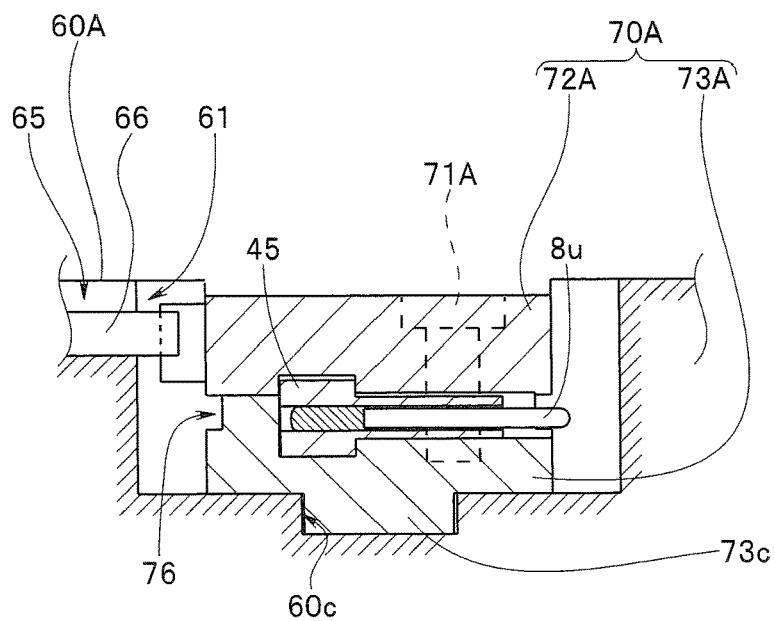
FIG. 9B is a diagram explaining assembly of the rotation adjusting member to the rotation body accommodating portion in a different configuration.

Then, as illustrated in FIG. 9B, a rotating main body 73A is configured by providing a projected portion 73c on a main body back surface center. The projected portion 73c is arranged in a recessed portion 60c formed on the bottom surface of the pulley 60A and configures a turning shaft.

The lid body 72A with the ratchet gear and the rotating main body 73A are integrally fixed by a fixing screw 71A and configure a rotation adjusting member 70A.

Note that a distal end of the fixing screw 71A is arranged inside the female screw hole 75 of the rotating main body 73A. The other configuration is similar to the configuration illustrated in FIG. 8A to FIG. 8C, same signs are attached to same members and the description is omitted.

Here, the assembly of the bending wires 8u and 8d to the pulley 60A will be described.

Note that a procedure of assembling the upper bending wire 8u to the pulley 60A will be described here, too, and for the assembly of the lower bending wire 8d to the pulley 60A in the similar assembly procedure, the description is omitted.

The operator first disposes the stepped pin 45 fixed to the second end of the upper bending wire 8u inside the fixing member disposing hole 74 of the rotating main body 73A. Next, the operator mounts the lid body 72A with the ratchet gear on the surface of the rotating main body 73A. As a result, the small diameter hole 78b and the female screw hole 75 are turned to the opposing positional relation and the rotation adjusting member 70A is configured. In addition, the step portion 76a is configured as the wire disposing groove 76, and the upper bending wire 8u is arranged inside the wire disposing groove 76.

Next, the operator disposes the rotation adjusting member 70A configured by screwing the two fixing screws 71A to the two female screw holes 75 of the rotating main body 73A through the screw holes 78 of the lid body 72A with the ratchet gear respectively inside the rotating body accommodating portion 61

At the time, by disposing the projected portion 73c in the recessed portion 60c as illustrated in FIG. 9B, the rotation adjusting member 70A including the upper bending wire 8u is turnably attached to the pulley 60A.

Next, the operator turnably attaches the rotation adjusting member 70A including the lower bending wire 8d to the pulley 60A similarly to the above description.

Thereafter, the operator adjusts the tension by arranging, for example, the distal end of the flathead screwdriver in the groove 77, rotating the rotation adjusting member 70A and increasing and decreasing the winding amount of the bending wires 8u and 8d. As a result, the tension of the upper bending wire 8u and the tension of the lower bending wire 8d can be adjusted to the predetermined state.

Then, in the present embodiment, the position after the tension adjustment is stably held by the ratchet mechanism, and the assembly of the bending wires 8u and 8d to the pulley 60A is completed.

Note that the present invention is not limited only to the embodiments described above, and various modifications can be executed without departing from a subject matter of the invention.

According to the present invention, the endoscope capable of adjusting the tension of the bending wire while setting the length of the operation portion body short can be realized.

What is claimed is:

1. An endoscope comprising:
    an insertion portion including a bending portion bendable at least in a vertical direction on a distal end portion side of the insertion portion;
    an operation portion to which a proximal end portion of the insertion portion is connected;

a traction wire including a first end and a second end, the traction wire being connected to the insertion portion at the first end, the traction wire being configured to bend the bending portion by being pulled;

a fixing member fixed to the second end of the traction wire;

a holding member configured to hold the fixing member; and a pulley turnably provided inside the operation portion and including a disposing portion where the holding member is disposed, wherein the pulley includes:

a screw receiving member disposing space as the disposing portion including a notched surface where a screw receiving member as the holding member to which a screw member as the fixing member is screwed and arranged is arranged, the screw receiving member disposing space being a notched portion formed such that a part of a disk of the pulley is notched as the pulley is viewed from a direction of a turning shaft of the pulley, and a through-hole that communicates a first opening formed on a bottom surface of a circumferential groove of the pulley and a second opening formed on the notched surface, wherein a proximal end portion of the traction wire is inserted into the through-hole, the proximal end portion including the second end, and the holding member holds the fixing member such that an arranging position of the holding member is adjustable with respect to the fixing member in the screw receiving member disposing space.

2. The endoscope according to claim 1, wherein tension of the traction wire is set to a predetermined state by adjusting an arranging position of the screw member screwed to the holding member.

3. The endoscope according to claim 2, wherein the screw receiving member and the screw member, and the screw receiving member and the notched surface are integrally fixed by an adhesive agent.

4. The endoscope according to claim 2, wherein the screw receiving member and the screw member, and the screw receiving member and the notched surface are integrally fixed by a heat-shrinkable tube.

* * * * *